United States Patent [19]

Madaras

[11] Patent Number: 5,280,722
[45] Date of Patent: Jan. 25, 1994

[54] METHOD AND APPARATUS FOR INDICATING DISBONDS IN JOINT REGIONS

[76] Inventor: Eric I. Madaras, 202 Aspen Blvd., Yorktown, Va. 23692

[21] Appl. No.: 751,489

[22] Filed: Aug. 29, 1991

[51] Int. Cl.$^5$ .................. G01N 29/10; G01N 29/28
[52] U.S. Cl. ........................... 73/588; 73/644
[58] Field of Search ............... 73/588, 600, 617, 620, 73/627, 640, 644, 632

[56] References Cited

U.S. PATENT DOCUMENTS

| | | | |
|---|---|---|---|
| 4,348,904 | 9/1982 | Bautista, Jr. | 73/644 |
| 4,807,476 | 2/1989 | Cook et al. | 73/620 |
| 4,848,159 | 7/1989 | Kennedy et al. | 73/588 |
| 4,866,986 | 9/1989 | Ciehanski | 73/600 |
| 4,901,729 | 2/1990 | Saitoh et al. | 128/662.03 |

FOREIGN PATENT DOCUMENTS

| | | | |
|---|---|---|---|
| 0266456 | 11/1987 | Japan | 73/627 |
| 0001955 | 1/1989 | Japan | 73/627 |

*Primary Examiner*—Hezron E. Williams
*Assistant Examiner*—Rose M. Finley

[57] ABSTRACT

A method and apparatus are provided for indicating disbonds in joint regions. A critical bondline region is located between a first material and a second material having a higher acoustic impedance than the first material. A form member having an acoustic impedance which is substantially similar to the first material has a first face which is form fitted to a surface of the first material opposite to and non-parallel with the critical bondline region. The form member has an opposite second face which is shaped to be parallel to the critcal bondline region. Transducers are acoustically coupled to the second face of the form member to generate an ultrasonic tone burst through the acoustically similar form member and first material which is reflected by the critical bondline region. This reflected tone burst is received and a resulting signal is compared with a normal signal for no disbond to determine the presence of an unacceptable disbond.

2 Claims, 3 Drawing Sheets

METHOD AND APPARATUS FOR INDICATING DISBONDS IN JOINT REGIONS

ORIGIN OF THE INVENTION

The invention described herein was made by an employee of the United States Government and may be manufactured and used by the Government for governmental purposes without the payment of any royalties thereon or therefor.

BACKGROUND OF THE INVENTION

1. Technical Field of the Invention

The present invention relates generally to disbond measuring and more particularly to a method of measuring disbonds in joint regions.

2. Discussion of the Related Art

Disbonds constitute a major threat to the structural integrity of a multi-element component. Visual inspection of the component for disbonds is often not possible since the joint regions are surrounded by other elements. Non-visual techniques such as tangential x-ray or ultrasound inspection have been unsuccessful in accurately detecting joint disbonds, especially in complex geometry joint areas such as those existing in solid rocket motors (SRMs). Specifically, artifacts such as fluorescence near the edges of the component prevent any meaningful application of tangential x-ray techniques. All previous attempts employing ultrasound have met with failure.

OBJECTS OF THE INVENTION

It is accordingly an object of the present invention to measure disbonds in joint regions.

It is another object of the present invention to measure disbonds in complex geometry joint regions.

It is a further object of the present invention to achieve the foregoing objects non-visually.

It is another object of the present invention to achieve the foregoing objects non-invasively.

It is a further object of the present invention to achieve the foregoing objects in a simple manner.

Additional objects are apparent from the drawings and specification which follow.

SUMMARY OF THE INVENTION

The foregoing and additional objects are obtained by a method and apparatus for measuring disbonds in a joint region according to the present invention. A critical bondline region is located between a first material and a second material having a higher acoustic impedance than the first material. A form member having an acoustic impedance which is substantially similar to the first material has a first face which is form fitted to a surface of the first material opposite to and non-parallel with the critical bondline region. The form member has an opposite second face which is shaped to be parallel to the critical bondline region. Transducers are acoustically coupled to the second face of the form member to generate an ultrasonic tone burst through the acoustically similar form member and first material which is reflected by the critical bondline region. This reflected tone burst is received and a resulting signal is compared with a normal signal for no disbond to determine the presence of an unacceptable disbond.

DETAILED DESCRIPTION OF THE INVENTION

Figure 1A:
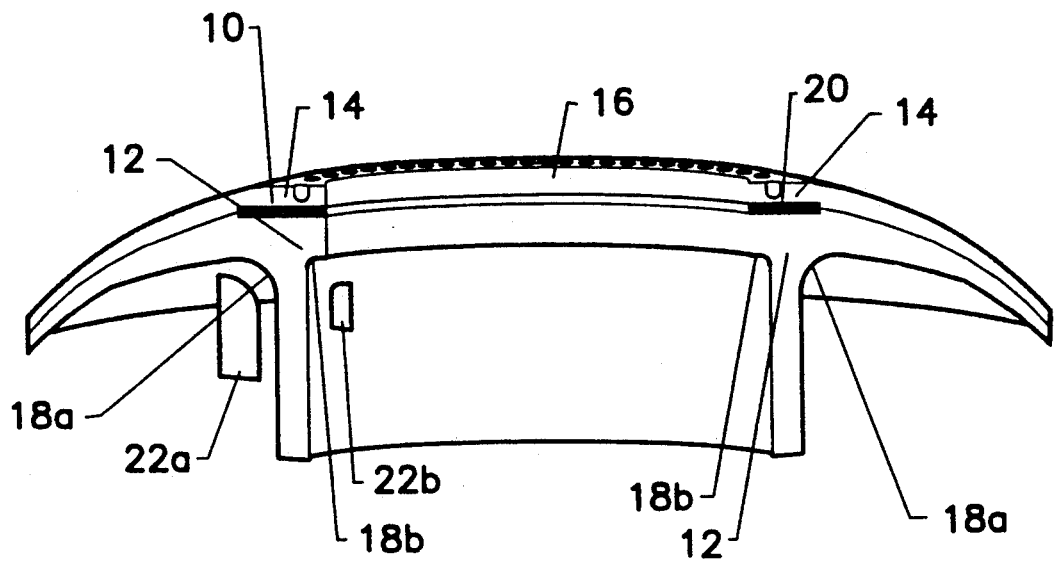
FIGS. 1a and 1b are respective exposed side views of the present invention showing uninstalled from blocks and installed from blocks and associated transducers.

Referring now to FIG. 1a, a complex geometry joint area 10 is shown between a first material 12 and a second material 14. For example, this complex geometry may constitute the forward dome to igniter seal of a solid rocket motor (SRM), wherein the first material 12 is NBR, or Acryl-Nitrile Buna Rubber, insulation material and the second material 14 is an exterior shell of D6AC steel. The curved geometry forms a receptacle 16 for installation of the SRM igniter (not shown). The particular geometry of the first material 12 depicted forms two arches respectively designated 18a and 18b, which are non-parallel to the face of first material 12 bonded to second material 14.

In conventional ultrasound techniques, transducers in a pulse/echo mode would be applied to the arches 18a and 18b in an attempt to measure the critical bondline region 20 located between the two materials. However, the complex geometry of the joint region 10 distorts any resulting ultrasound picture of the bondline region.

To avoid this problem, the present invention contemplates fitting respective compensating form members 22a and 22b with the arches 18a and 18b of the first material 12, e.g., insulation. The form members are selected to have approximately the same acoustic properties, e.g., acoustic impedance, as the first material. For example, if the first material 12 is a particular insulation, then the form members may be an acoustically similar insulation or polymer. Each form member comprises at least two opposite faces. The first face of each form block is formed to fit the contours of the opposing geometry of the first material, e.g., the respective arch depicted. The second face is formed to be parallel with the critical bondline region 20 when the form member is fitted to the first material 12. This fitting is accomplished with any suitable couplant, preferably such that no acoustic interference is induced. Transducers 24a and 24b are then acoustically coupled to the respective second face of the form member which is facing, i.e., parallel with, the bondline region 20. See FIG. 1b.

The described redefinition of the shape of the first material 12 results in a simple geometry which facilitates ultrasound measurements. The transducer is operated in a pulse/echo mode whereby an ultrasonic tone burst is transmitted from the respective transducer, through the associated form block and first material 12 having similar acoustic properties, and contacts the second material 14 at the critical bondline region 20. The tone burst is reflected back through the first material 12 and associated form block and the echo is then received by the transducer.

By insonifying the bondline region 20 from the insulative first material side having a lower acoustic impedance than the steel second material, the difference between a disbond and an acceptable bond will cause the returning tone burst echo to exhibit a phase inverted transducer signal compared to the phase of a transducer signal indicating an acceptable bond. This phase inversion is a more reliable indication of disbond than a change in signal amplitude. By employing two transducers in the pulse/echo mode, the outer portions of the critical bondline region 20 can be examined for disbonds.

Figure 1B:
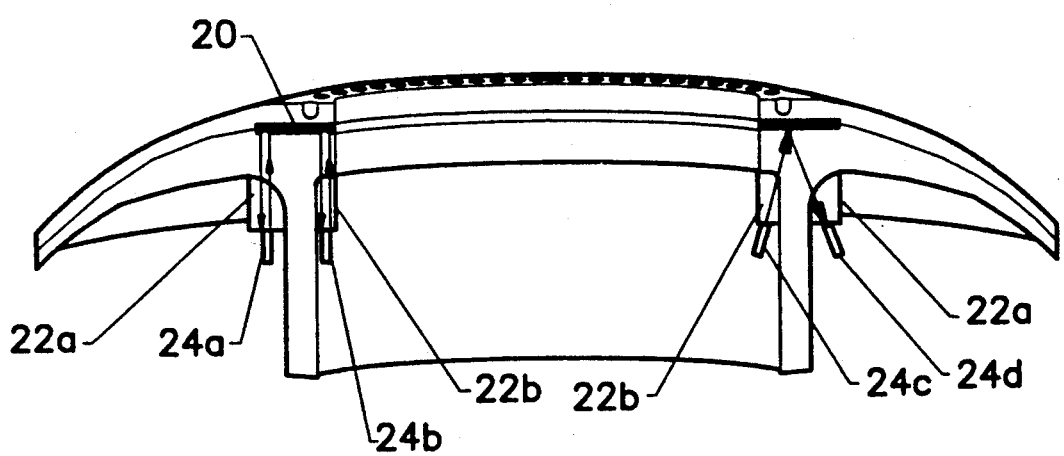

A pair of transducers can also be operated in a pitch/catch mode, as shown in FIG. 1b. Transducer 24c transmits the tone burst and transducer 24d receives the echo. This transducer configuration allows the central portion of critical bondline region 20 to be ultrasonically evaluated. This central portion would otherwise be inaccessible due to the presence of the protruding section of the first material 12. For transmission (pitch) and reception (catch) along a path which deviates from the perpendicular axis extending from bondline region 20, best results are achieved using respective wedge-shaped face plates (not shown) between each transducer 24c and 24d and the associated form member 22b and 22a. The transducers 24c and 24d can be reconfigured in the same arrangement as transducers 24a and 24b and operated in the pulse/echo mode to evaluate the remaining outer portions of the critical bondline region 20.

Once the measurements are performed, the transducers and form members are removed from the first material. Depending on the evaluation, the joint is then either repaired or approved for service.

Figure 2A:
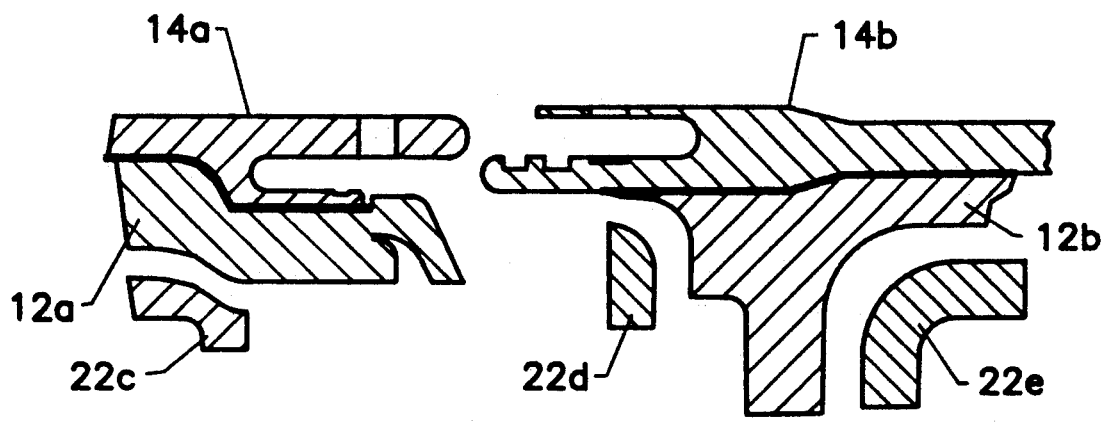
FIGS. 2a, 2b, and 2c are respective exposed side views of the present invention as applied to a tang-clevis arrangement.
Figure 2B:
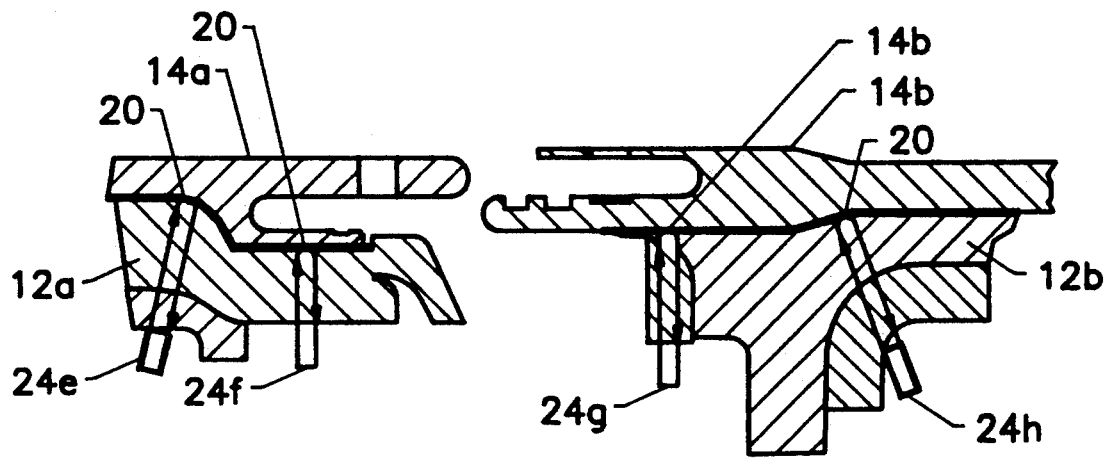
Figure 2C:
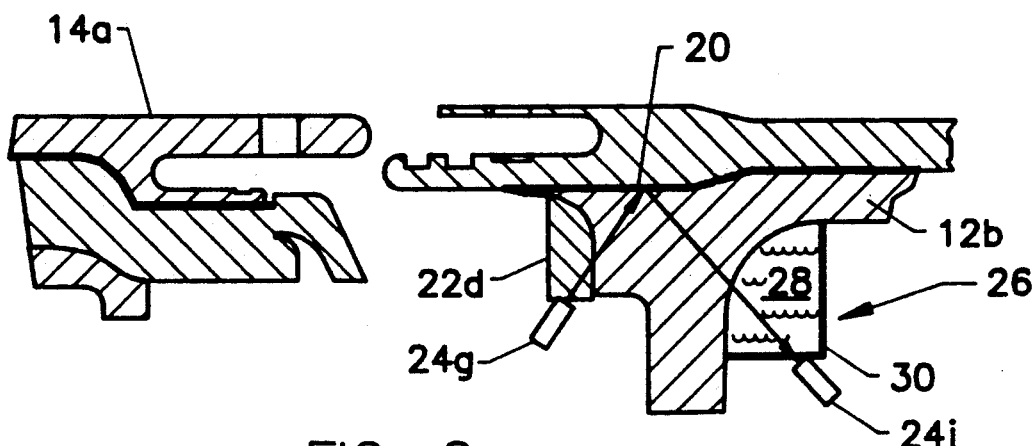

Referring now to FIGS. 2a-c, the measurement method according to the present invention is applied to a tang and clevis field joint. A tang 14a and a clevis 14b are fabricated from the second material. Insulation 12a and 12b, comprised of the first material, is respectively bonded to the tang 14a and clevis 14b. As before, critical bondline regions 20 exist between the first and second materials. Form members 22c, 22d, and 22e are respectively fitted to the insulation 12a and 12b respectively bonded to the tang 14a and clevis 14b. Once again, the form members have an acoustic impedance which is substantially similar to that of the insulating first material, e.g., the form members are comprised of the same insulating material or a polymer. One face of each form member corresponds to the contour of the first material opposite the critical bondline region 20. The opposite face of each form member form is shaped such that a simple geometrical structure is formed from the first material and the form member. In this context, simple geometry is defined to encompass a shape which permits ultrasonic evaluation of the critical bondline region 20. More specifically, the opposite face of each form member should be shaped such that it is parallel with the particular critical bondline region 20, i.e., such that the ultrasonic tone burst from the associated transducer impinges perpendicularly on the critical bondline region.

As before, transducers 24e, 24g and 24h are affixed to this opposite face of an associated form member and are operated in a pulse/echo mode to evaluate the associated critical bondline region 20 ultrasonically. Transducer 24f, operated in pulse/echo mode, is coupled directly to the insulating first material 12a of tang 14a since this portion of the first material is parallel with its associated critical bondline region 20. To evaluate portions of a critical bondline region which is inaccessible via a perpendicular path from the form member to the region, two transducers, e.g., transducers 24i and 24j, can be operated in a pitch/catch mode as discussed previously.

The present invention thus allows complex geometry, critical bondline regions to be evaluated ultrasonically. The illustrative example described above use a preformed solid as the form member. This necessitates careful modeling of the form member to fit the contour of the first material. To avoid this step, a flexible form member 26 is employed comprising a flexible bay 28 which is partially encased by a frame member 30, as shown in FIG. 2c. Bay 28 and frame member 30 should be constructed of materials which do not affect the transmission of the ultrasonic tone burst. For example, bay 28 may be filled with water which is similar in acoustic impedance to rubber or certain plastics and is relatively non-absorbent to acoustic energy compared to rubber or certain plastics. The flexible face of bay 28 may be a tough, thin rubber or plastic bladder. Neither the water nor the thin bladder would appreciably affect the transmission of the ultrasonic tone burst in a negative fashion yet the system would conform to the surface shape of first material as desired.

Figure 3:
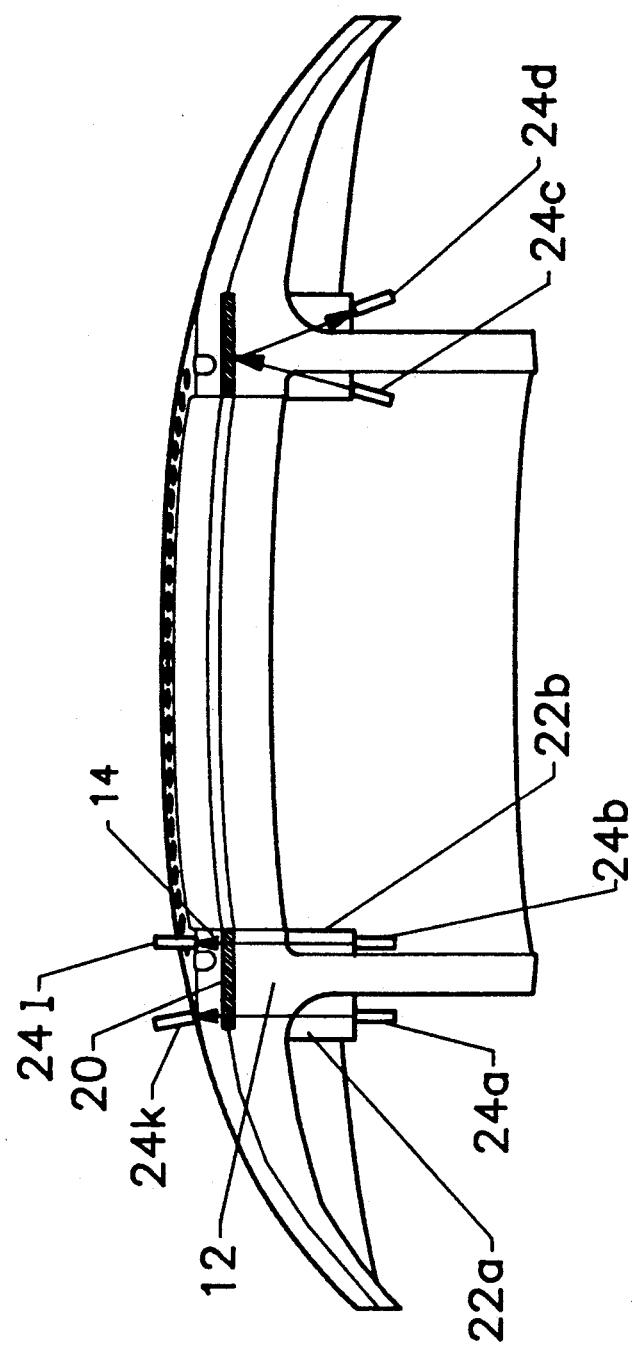
FIG. 3 is an embodiment showing an embodiment using pitch/catch through transmission.

The transducers can also be arranged to measure the sound which is transmitted through the form member, first material, critical bondline region and the second material, as shown in FIG. 3. A first transducer 24a, 24b is acoustically coupled to the form member as above and a second transducer 24k, 24l is acoustically coupled to the second material. The paired transducers are operated in a pitch/catch mode from the first to the second transducer and a change in the amplitude of the signal, rather than a change in phase, is used to indicate an unacceptable bondline when the change exceeds an established value. This amplitude detector is used in the pitch/catch mode when the signal is a through transmission with no reflections. Through transmission is reliable provided that the angle of entrance and the angle of exit of the acoustic wave with respect to the second material 14 is not excessive, i.e., below the critical angle where total reflection occurs.

Many modifications, substitutions and improvements will be apparent to the skilled artisan without departing from the spirit and scope of the present invention as described herein and defined in the following claims.

What is claimed is:

1. A method of identifying disbonds in a joint comprising a first material bonded to a second material with a critical bondline region therebetween, the first material having a surface opposite to and non-parallel with the critical bondline region, wherein the first material has a lower acoustic impedance than the second material, the method comprising the steps of:

fitting a first face of a form member to the surface of the first material opposite to and non-parallel with the critical bondline region, the form member having an acoustic impedance which is similar to the first material, the form member having a second face opposite the first face and which is arranged parallel with the critical bondline region;

acoustically coupling a transducer to the second face of the form member; and applying an ultrasonic tone burst to the second face of the form member via the transducer which travels through the form member, first material and critical bondline region and is reflected by the second material, whereby the reflected tone burst is indicative of a presence of disbonds in the critical bondline region.

2. An article for use in identifying a disbond in a critical bondline region joining a first material and a second material, wherein the first material has a lower acoustic impedance than the second material, and wherein the first material has a surface opposite to and non-parallel with the critical bondline region, the article comprising:

a form member having an acoustic impedance which is similar to the acoustic impedance of the first material, the form member having a first face which conforms to the surface of the first material opposite to and non-parallel with the critical bondline region, the form member having a second face opposite the first face which is parallel with the critical bondline region, whereby a transducer may be acoustically coupled to the second face.

* * * * *